United States Patent
Georgeson et al.

(10) Patent No.: US 9,915,633 B2
(45) Date of Patent: Mar. 13, 2018

(54) TWO-DIMENSIONAL ARRAY DEPRESSION PROFILER AND MEASUREMENT DEVICE

(71) Applicant: The Boeing Company, Chicago, IL (US)

(72) Inventors: Gary E. Georgeson, Tacoma, WA (US); Tyler M. Holmes, Seattle, WA (US); Jeffrey R. Kollgaard, Seattle, WA (US)

(73) Assignee: The Boeing Company, Chicago, IL (US)

( * ) Notice: Subject to any disclaimer, the term of this patent is extended or adjusted under 35 U.S.C. 154(b) by 294 days.

(21) Appl. No.: 14/811,735

(22) Filed: Jul. 28, 2015

(65) Prior Publication Data

US 2017/0030864 A1  Feb. 2, 2017

(51) Int. Cl.
| | |
|---|---|
| *G01N 29/07* | (2006.01) |
| *G01N 29/11* | (2006.01) |
| *G01N 29/24* | (2006.01) |
| *G01N 29/30* | (2006.01) |
| *G01N 29/44* | (2006.01) |

(Continued)

(52) U.S. Cl.
CPC ........... *G01N 29/041* (2013.01); *G01N 29/07* (2013.01); *G01N 29/11* (2013.01); *G01N 29/2468* (2013.01); *G01N 29/28* (2013.01); *G01N 29/30* (2013.01); *G01N 29/4445* (2013.01); *G01N 2291/0231* (2013.01);
(Continued)

(58) Field of Classification Search
CPC .. G01N 29/041; G01N 29/4445; G01N 29/07; G01N 29/11; G01N 29/28; G01N 29/30; G01N 2291/106; G01N 2291/0234

USPC .......................................................... 73/632
See application file for complete search history.

(56) References Cited

U.S. PATENT DOCUMENTS 5,494,038 A * 2/1996 Wang .................. A61B 8/0866
600/459
7,617,730 B2   11/2009 Georgeson
(Continued)

OTHER PUBLICATIONS

Allard et al., Improvement of aircraft mechanical damage inspection with advanced 3D imaging technologies, 5th International Symposium on NDT in Aerospace, Nov. 19, 2013.
(Continued)

*Primary Examiner* — J M Saint Surin
(74) *Attorney, Agent, or Firm* — McDonnell Boehnen Hulbert & Berghoff LLP/Boeing (57) ABSTRACT

Example systems and methods for non-destructive evaluation of depressions on a surface of an object are provided. One example system includes a measurement apparatus having a two-dimensional ultrasonic transducer array, a delay line material, a sealing member position such that the sealing member forms a cavity between the delay line material and a surface of the object, and a liquid inlet for injecting a liquid into the cavity. The example system also includes a processor configured to determine, using ultrasonic signals received from the two-dimensional ultrasonic transducer array, at least one property of a depression such as a dent on the surface of an object. The example system may also be configured to provide an output that is indicative of whether the at least one property of the depression satisfies a predetermined criterion. Another example system includes a compressible elastomeric delay line material that conforms to a surface of an object.

20 Claims, 8 Drawing Sheets

(51) Int. Cl.
 *G01N 29/04* (2006.01)
 *G01N 29/28* (2006.01)
(52) U.S. Cl.
 CPC ............... *G01N 2291/0234* (2013.01); *G01N 2291/106* (2013.01); *G01N 2291/2694* (2013.01)

(56) References Cited

U.S. PATENT DOCUMENTS

| | | | |
|---|---|---|---|
| 7,712,369 B2 | 5/2010 | Georgeson | |
| 8,453,928 B2 | 6/2013 | Melandso et al. | |
| 8,662,395 B2 | 3/2014 | Melandso et al. | |
| 9,664,652 B2* | 5/2017 | Fetzer | G01N 29/265 |
| 9,689,844 B2* | 6/2017 | Holmes | G01N 29/041 |
| 2004/0248425 A1* | 12/2004 | Bem | B05C 5/001 438/758 |
| 2007/0084290 A1* | 4/2007 | Fetzer | G01N 29/0645 73/627 |
| 2008/0053230 A1* | 3/2008 | Katsura | G01N 29/043 73/571 |
| 2008/0309200 A1 | 12/2008 | Melandso et al. | |
| 2011/0072905 A1* | 3/2011 | Lam | G01N 29/221 73/622 |

OTHER PUBLICATIONS

MoireView: The optical system for dent analysis, Testia, available at www.testia.com/documents/1-MoireView.pdf, Jun. 10, 2014.

* cited by examiner

TWO-DIMENSIONAL ARRAY DEPRESSION PROFILER AND MEASUREMENT DEVICE

FIELD

The present disclosure relates generally to ultrasonic systems and methods for inspecting structures, and more particularly, to ultrasonic systems and methods for evaluating surface depressions on structures.

BACKGROUND

Modern aerospace structures are susceptible to mechanical surface damage. For example, hailstorms can damage an aircraft's fuselage, wings, or other structures while the aircraft is in flight or on the ground. Similarly, incidental contact with various ground objects can mechanically damage the surface of one or more structures of an aircraft or other type of aerospace structure. After the surface of one of an aircraft's structures is damaged, an inspector must evaluate any damage such as depressions including "dents" on the surface to determine whether the structure conforms to a manufacturer's or regulator's requirements. This process may involve measuring the depth or width of each dent and then dispositioning each dent as having an acceptable or unacceptable profile. In some cases, if a dent is sufficiently large or deep, repairs may need to be made.

Various approaches to measuring the depth or width of a surface dent on an aerospace structure exist. According to one approach, an inspector manually measures the depth and width of dents using a scale and a dial indicator gauge. Other approaches make use of laser line gauges or laser profilometry systems. Further, other approaches use interferometric devices that operate based on the moiré effect.

SUMMARY

In one example, a system for non-destructive evaluation of depressions on a surface of an object is provided. The system comprises a measurement apparatus and a processor. The measurement apparatus comprises a two-dimensional ultrasonic transducer array and a delay line material coupled to the two-dimensional ultrasonic transducer array. The measurement apparatus also comprises a sealing member positioned such that the sealing member forms a cavity between the delay line material and the surface of the object when the measurement apparatus is placed onto the surface of the object. Further, the measurement apparatus comprises a liquid inlet for injecting a liquid into the cavity. The processor is configured to determine, using ultrasonic signals received from the two-dimensional ultrasonic transducer array, at least one property of a depression on the surface of the object.

In another example, another system for non-destructive evaluation of depressions on a surface of an object is provided. The system comprises a measurement apparatus and a processor. The measurement apparatus comprises a housing having an opening, and comprises a two-dimensional ultrasonic transducer array positioned within the housing. The measurement apparatus also comprises an elastomeric delay line material coupled to the two-dimensional ultrasonic transducer array. The elastomeric delay line material has a contact face configured to contact the surface of the object, and the contact face of the elastomeric delay line material protrudes through the opening of the housing when the elastomeric delay line material is in a relaxed state. Further, the elastomeric delay line material is compressible toward the two-dimensional ultrasonic transducer array when the measurement apparatus is placed onto the surface of the object. The processor is configured to determine, using ultrasonic signals received from the two-dimensional ultrasonic transducer array, at least one property of a depression on a surface of the object.

In still another example, a method for non-destructive evaluation of depressions on a surface of an object is provided. The method includes placing a measurement apparatus comprising a two-dimensional ultrasonic transducer array onto the surface of the object. The method also includes transmitting from each of a plurality of ultrasonic transducers of the two-dimensional ultrasonic transducer array an ultrasonic pulse toward the surface of the object. Additionally, the method includes receiving by one or more of the plurality of ultrasonic transducers one or more ultrasonic echoes resulting from the transmitting of the ultrasonic pulses. Further, the method includes determining, by a processor and using the received ultrasonic echoes, at least one property of a depression on the surface of the object. Yet further, the method includes determining, by the processor, whether the at least one property satisfies a predetermined criterion. And the method includes causing, by the processor, an output component to provide an output that is indicative of whether the at least one property of the depression satisfies the predetermined criterion.

The features, functions, and advantages that have been discussed can be achieved independently in various embodiments or may be combined in yet other embodiments further details of which can be seen with reference to the following description and figures.

BRIEF DESCRIPTION OF THE FIGURES

The novel features believed characteristic of the illustrative embodiments are set forth in the appended claims. The illustrative embodiments, however, as well as a preferred mode of use, further objectives and descriptions thereof, will best be understood by reference to the following detailed description of an illustrative embodiment of the present disclosure when read in conjunction with the accompanying figures, wherein:

DETAILED DESCRIPTION

Disclosed embodiments will now be described more fully hereinafter with reference to the accompanying figures, in which some, but not all of the disclosed embodiments are shown. Indeed, several different embodiments may be provided and should not be construed as limited to the embodiments set forth herein. Rather, these embodiments are provided so that this disclosure will be thorough and complete and will fully convey the scope of the disclosure to those skilled in the art.

To help illustrates features of the present disclosure, portions of this disclosure focus on an aircraft structure, by way of example. Those of ordinary skill in the art will readily appreciate, however, that the disclosed principles can be applied as well to other aerospace structures or similar structures, with variations where appropriate.

Within examples, ultrasonic systems and methods for evaluating surface damage on structures are provided. In some examples, the systems and methods may facilitate accurately measuring a number of different depressions, such as dents, on a surface of an object, and quickly dispositioning each depression as having an acceptable or unacceptable depth and/or contour. For instance, the systems and methods described herein may enable an inspector to rapidly evaluate depressions on an aircraft structure in a scenario in which the aircraft is temporarily grounded due to damage stemming from a hailstorm or other event.

Advantageously, the systems and methods disclosed herein may enable an inspector to evaluate the damage to an aircraft structure more quickly than evaluating the damage using other approaches (e.g., via scale and dial indicator gauge, laser profilometry, or interferometric device), thereby accelerating the aircraft's return to service and reducing downtime. Further, the systems disclosed herein may be more cost effective to manufacturer than systems using laser profilometry or interferometry. In addition, the systems disclosed herein may automatically classify a depression on a surface of an object as being acceptable or requiring repair.

In many ultrasonic inspection applications, ultrasonic technology is used to detect material thinning in metals or composites. Some of the systems and methods disclosed herein use ultrasonic technology in a similar manner to detect liquid path differences in a layer of liquid. Because the speed of sound is slower in liquids than in metals or composites, depth resolution is easier to achieve when applying ultrasonic technology to liquids than when applying ultrasonic technology to metals or composites. Other example systems and methods disclosed herein detect path differences in a semi-solid delay line material through which the speed of sound is also lower than the speed of sound in metals or composites. A delay line material is a layer of material that delays ultrasonic pulses traveling through the layer. As the name implies, the delay line material may introduce a time delay between a generation of an ultrasonic pulse and an arrival of any reflected ultrasonic echoes. In addition to the advantages related to the speed of sound, the reflection coefficient of ultrasound between a liquid and an aircraft structure, for instance, or between a semi-solid delay line material and an aircraft structure, is sufficient to generate an ultrasonic wave having an acceptable signal-to-noise ratio, such that the ultrasonic wave may be used to produce a depth measurement.

In accordance with embodiments disclosed herein, an example system includes a measurement apparatus and a processor. The measurement apparatus includes a two-dimensional ultrasonic transducer array that may be configured for measuring the distance to a surface of an object at multiple different points on the surface. Since the measurement apparatus includes a two-dimensional ultrasonic transducer array, the measurement apparatus may be used to create volumetric data including depth values (i.e., z values) for a matrix of positions on the surface of the object (i.e. x-y positions). The processor can then use the volumetric data to construct a virtual representation of the surface. Alternatively, the processor may use the volumetric data as input to one or more logical operations for classifying a depression as acceptable or unacceptable. As a particular example, the processor may compare the depth values to a depth threshold. If a single depth value exceeds the depth threshold, or if more than a predetermined number of depth values exceed the depth threshold, the processor may provide an output that indicates the depression is unacceptable. Based on the output, an operator of the system may then mark the depression for repair, and proceed to evaluate additional damage, such as another depression on the surface of the object.

As discussed below, in some instances, the measurement apparatus may also be used to inspect an internal structure beneath a surface depression. For example, in addition to depth values corresponding to positions on the surface of the object, the measurement apparatus may also be configured to image and analyze damage or deformations below the surface. The processor may then provide a virtual representation of the surface and the interior of the structure below the surface.

In one embodiment, the measurement apparatus may include a delay line material coupled to the two-dimensional ultrasonic transducer array. Further, the measurement apparatus may include a sealing member positioned such that that the sealing member forms a cavity between the delay line material and the surface of the object when the measurement apparatus is placed onto the surface of the object. After the measurement apparatus is placed onto the surface of the object, forming the cavity, an operator may inject a liquid into the cavity using a liquid inlet. Once the cavity is filled, the operator may push a button that causes each of a plurality of ultrasonic transducers of the two-dimensional ultrasonic transducer array to transmit an ultrasonic pulse toward the surface of the object through the delay line material and the liquid. The two-dimensional ultrasonic transducer array may then receive one or more ultrasonic echoes resulting from the transmitting of the ultrasonic pulses, and relay the ultrasonic echoes to the processor for processing.

In another embodiment, the measurement apparatus may include an elastomeric delay line material coupled to the two-dimensional ultrasonic transducer array. The elastomeric delay line material may have a contact face that protrudes from an opening of the measurement apparatus and is configured to contact a surface of an object. When the measurement apparatus is applied to the surface of the object, the contact face of the elastomeric delay line material may conform to the surface of the object. For instance, a portion of the elastomeric delay line material overlaying a depression on the surface may enter into and fill in the depression, while portions of the elastomeric delay line material adjacent to the depression may compress toward the two-dimensional transducer array. An operator may then push a button that causes each of a plurality of ultrasonic transducers of the two-dimensional ultrasonic transducer array to transmit an ultrasonic pulse toward the surface of object through the elastomeric delay line material. The two-dimensional ultrasonic transducer array may then receive one or more ultrasonic echoes resulting from the transmitting of the ultrasonic pulses, and relay the ultrasonic echoes to the processor for processing.

In some examples, compression of the elastomeric delay line material may change the speed of sound in the elastomeric delay line material. This change in speed of sound can be taken into account during processing of the ultrasonic echoes. For instance, the change in speed of sound due to compression can be calculated by calibrating the measurement apparatus using a reference depression standard. The calibration may yield a calibration curve, and the change in speed of sound due compression may then be accounted for using the calibration curve.

In some instances, the measurement apparatuses disclosed herein may be calibrated using a depression standard. Such a depression standard may be stored with a measurement apparatus, for instance, for use in pre-test calibration of the measurement.

Various other features of the example systems discussed above, as well as methods for evaluating a surface of an object using these systems, are also described hereinafter with reference to the accompanying figures.

Figure 1:
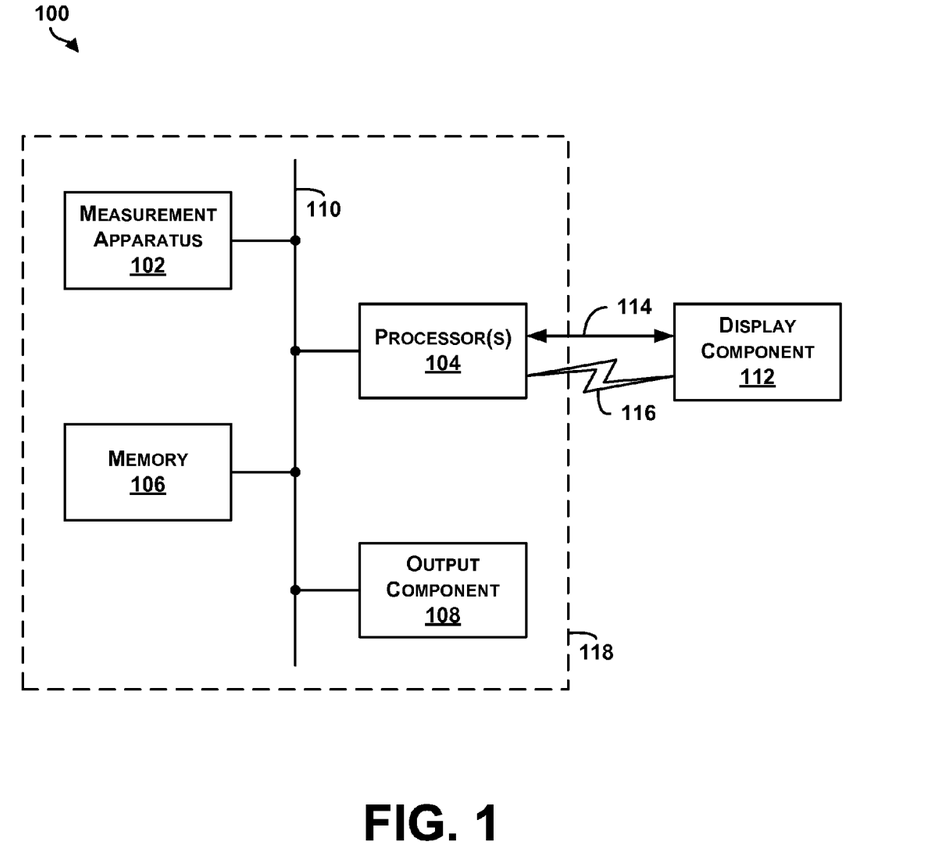
FIG. 1 is a schematic diagram of an example system according to an example embodiment.

Referring now to the figures, FIG. 1 is a schematic diagram of an example system 100. In line with the discussion above, the example system 100 may be used to inspect the surface of a structure, such as an aircraft structure or component. As shown in FIG. 1, the example system 100 includes a measurement apparatus 102, one or more processors 104, a memory 106, and an output component 108, all of which may be coupled together by a system bus, network, or other connection mechanism 110.

As discussed above, measurement apparatus 102 may include a two-dimensional ultrasonic transducer array (not shown). The two-dimensional ultrasonic transducer array may include ultrasonic transducers arranged in a regularly spaced pattern. In one example, each ultrasonic transducer may be operable as a pulse-echo inspection sensor that both sends and receives ultrasonic waves. The ultrasonic transducers can be fabricated, for example, from a polymer-based piezo-electric material called polyvinylidene fluoride (PVDF). Depending on the desired configuration, the two-dimensional transducer array may include different numbers of ultrasonic transducers. As one example, the two-dimensional transducer array may include two hundred and fifty-six transducers disposed in rows and columns regularly spaced by one quarter of one inch to define a square grid pattern that is four inches wide on each side thereof. In other examples, the ultrasonic transducers may be arranged in another two-dimensional pattern, such as a hexagonal pattern or other pattern.

In another example, the two-dimensional ultrasonic transducer may be a two-dimensional matrix array. In one embodiment, the two-dimensional matrix array may be built up of a number of elongated, parallel driving (or transmitting) electrodes arranged on one surface of a transducer plate and a plurality of parallel receiving electrodes arranged on an opposite surface of the transducer plate. The driving electrodes and the receiving electrodes may intersect to form a matrix of individual transducer elements capable of emitting and receiving ultrasonic waves. Other configurations of intersecting, overlaying elongated electrodes are also possible. In some instances, using the two-dimensional matrix array as opposed to a plurality of ultrasonic transducers arranged in a single plane may be more cost effective and involve less connectors and electronics.

The one or more processors 104 may function to control the two-dimensional ultrasonic transducer array and function to process ultrasonic signals received from the two-dimensional ultrasonic transducer array. As such, the one or more processors 104 may be any type of processor, such as a microprocessor, digital signal processor, multicore processor, etc. In one example, the one or more processors 104 may be coupled to an array controller (not shown) that functions to control the two-dimensional ultrasonic transducer array. The array controller may energize each ultrasonic transducer of the two-dimensional ultrasonic transducer array to send an ultrasonic pulse toward the surface of an object. The array controller may then receive an ultrasonic signal from the ultrasonic transducer when an ultrasonic echo returns and is received by the ultrasonic transducer.

Ultrasonic pulses tend to reflect from surfaces, edges, and other discontinuities between materials. The ultrasonic signals generated by each of the ultrasonic transducers may convey amplitude and time data corresponding to the amplitudes and arrival times of received ultrasonic echoes. Accordingly, a distance to a front surface of an object can be measured in one of two ways. In one example, one of the processors 104 may analyze an ultrasonic signal to measure the echo return time between: (i) a time when an initial ultrasonic pulse was transmitted and (ii) a time when an ultrasonic echo returns from the front surface of the object. In another example, one of the processors 104 may analyze an ultrasonic signal to measure a time difference between: (i) a time when an ultrasonic echo returns from an end of a delay line material and (ii) a time when an ultrasonic echo returns from the front surface of the object. Similarly, a distance to damage beneath the surface of the object can be determined by analyzing ultrasonic echoes returning from damage within the interior of the object. Generally, ultrasonic echoes indicative of damage within the interior of the object may be received after ultrasonic echoes returning from the front surface of the object.

When the measurement apparatus is disposed against a surface of an object, the data collected using the ultrasonic transducers can be associated with localized properties of the surface or interior of the object at the respective ultrasonic transducer locations. In one example, the array controller may maintain operations of each ultrasonic transducer separate in time from operations of each other ultrasonic transducer. This may help reduce cross-talk among the ultrasonic transducers.

The one or more processors 104 may be coupled to the memory 106. The memory 106 may be any type of memory, such as volatile memory like random access memory (RAM), dynamic RAM (DRAM), static RAM (SRAM), or non-volatile memory like read-only memory (ROM), flash memory, magnetic or optical disks, or compact-disc read-only memory (CD-ROM), among other devices used to store data or programs on a temporary or permanent basis.

In one example, the memory 106 may function to store ultrasonic signals received from the two-dimensional ultrasonic transducer array. In another example, the memory 106 may function to store volumetric data including depth values (i.e., z values) for a matrix of positions on the surface of the object (i.e. x-y positions) and/or below the surface of the object. Further, the memory 106 may function to store virtual representations of the surface of the object and/or interior structure of the object constructed by the one or more processors 104. Still further, the memory 106 may function to store program instructions executable by the one or more processors 104 to carry out various functions, such as using received ultrasonic signals to determine at least one property of a depression on a surface of the object and determining whether the at least one property of the depression satisfies a predetermined criterion.

Output component 108 may function to provide an output that is indicative of whether at least one property of a depression satisfies a predetermined criterion. As such, the output component 108 may comprise a light source (e.g., a light emitting diode) that is configured to provide a green or red light, depending on whether the depression satisfies a predetermined criterion. Alternatively, the output component 108 may comprise an electroacoustic transducer (e.g., a speaker) that is configured to provide an audible noise or alarm when a depression does not satisfy a predetermined criterion. The output component 108 may take other forms as well.

As further illustrated in FIG. 1, in some examples, the system 100 may further include a display component 112 that is coupled to the one or more processors 104 via a wired connection 114 or a wireless connection 116. The display component 112 may function to display ultrasonic signals received from the measurement apparatus 102. For instance, the display component 112 may display waveform plots indicative of the received ultrasonic signals. Additionally or alternatively, the display component 112 may display virtual representations of surfaces of objects, such as virtual representations indicative of the distances to various points on the surface of an object and/or damage beneath the surface of the object. In another example, the display component 112 may display one or more properties of a depression on a surface of the object, such as a maximum depth, average depth, width, width over depth ratio, etc. Further, in some examples, like the output component 108, the display component 112 may display an output that is indicative of whether at least one property of the depression satisfies a predetermined criterion.

In some examples, one or more of the measurement apparatus 102, processors 104, memory 106, and output component 108 may be part of an inspection device 118. By way of example, the inspection device 118 may be a handheld device. In operation, an operator may place the handheld device over a depression on a surface of a structure and use the handheld device to inspect the depression. After inspecting the depression, the operator may then relocate the handheld device to other damage, such as another depression on the surface of the structure. As another example, the inspection device 118 may be a robotic inspection device. For instance, the robotic inspection device may include a robotic arm configured to hold and manipulate or position the measurement apparatus 102, or the robotic inspection device may include a crawler or rover that is configured to move the measurement apparatus over an inspection surface.

In some instances, the display component 112 may also be part of the inspection device 118 (not shown). Alternatively, the display component 112 may be part of a stationary or mobile computing device, such as a tablet computing device, laptop computing device, or desktop computing device.

Figure 2A:
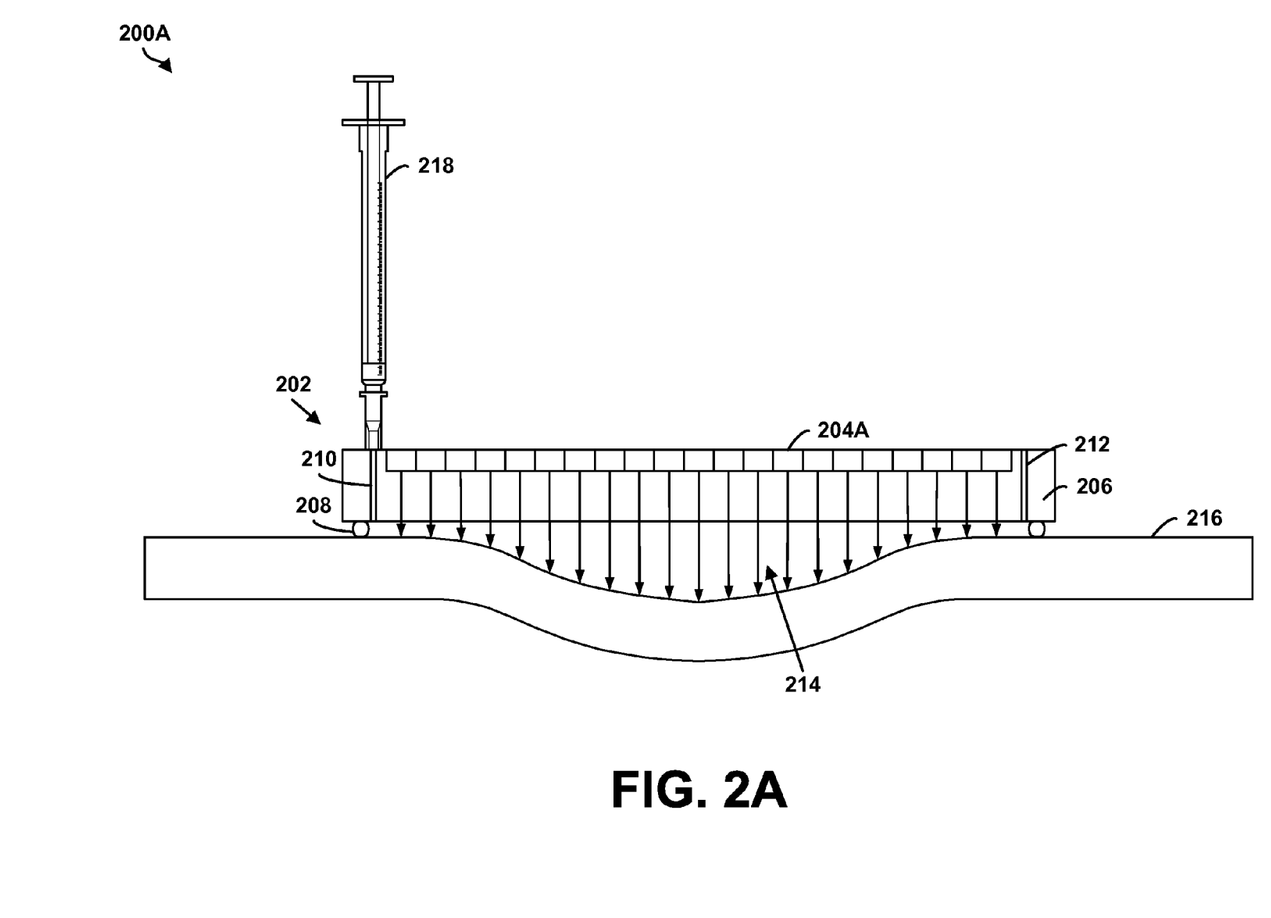
FIGS. 2A and 2B are conceptual illustrations of example systems according to an example embodiment.

As discussed above, in one example, the measurement apparatus 102 may be configured to couple to the surface of an object using a liquid couplant that facilitates the transmission of sound energy between the two-dimensional ultrasonic transducer array and the surface of the object. FIG. 2A is an illustration of an example liquid-coupled system 200A.

As shown in FIG. 2A, the example system 200A includes a measurement apparatus 202 having a two-dimensional ultrasonic transducer array 204A, a delay line material 206, a sealing member 208, a liquid inlet 210, and a liquid exhaust outlet 212.

Because the illustration of FIG. 2A is a cross-sectional view, only a single row of ultrasonic transducers of the two-dimensional ultrasonic transducer array 204A is visible. However, the two-dimensional ultrasonic transducer array 204A includes multiple rows of ultrasonic transducers.

In one example, the delay line material 206 may be a thermoplastic, such as poly(methyl methacrylate) (PMMA) which is also known as Lucite. In another example, the delay line material may be Rexolite, a translucent plastic produced by cross linking polystyrene with divinylbenzene. Other types of materials having similar acoustic properties may also be used for the delay line material 206.

The sealing member 208 may function to form a cavity 214 between the delay line material 206 and the surface of an object 216 when the measurement apparatus 202 is applied to the surface of the object 216. By way of example, the sealing member 208 may be an O-ring or a blade seal.

In operation, an inspector may apply the measurement apparatus 202 to the surface of the object 216, forming the cavity 214 between the delay line material 206 and the surface of the object 216. The operator may then inject a liquid into the cavity 214 using a liquid injector 218. In the example system of 200, the liquid injector 218 is depicted as a syringe that is configured to inject liquid into the cavity 214 via the liquid inlet 210. Other types of liquid injectors, such as a liquid injector having an external pump connected to a liquid source may also be used. Generally, the liquid may be any liquid that facilitates the transmission of sound energy between the delay line material 206 and the surface of the object 216. As one example, the liquid may be water. As another example, the liquid may be propylene glycol.

Once the cavity 214 is filled with the liquid, injecting additional liquid into the cavity 214 may cause liquid to exit the cavity 214 via the liquid exhaust outlet 212. For instance, the liquid exhaust outlet 212 may have a check valve that is designed to allow liquid to exit the cavity 214 when the cavity is overfilled.

After the cavity 214 is filled, the inspector may then press a button or otherwise trigger the ultrasonic transducers of the two-dimensional ultrasonic transducer array 204 to transmit ultrasonic pulses toward the surface of the object 216 through the delay line material 206 and the liquid within the cavity 214. Ultrasonic signals received from the two-dimensional ultrasonic transducer array 204 may then be stored and processed to construct a virtual representation of the surface and/or interior of the object 216 or to classify a depression on the surface of the object 216 as acceptable or unacceptable and provide an output indicative of the classification.

In one example, for each of the ultrasonic transducers of the ultrasonic transducer array 204, a processor of the system 200 (not shown) may measure an echo return time between (i) a time when an initial ultrasonic pulse was transmitted by the ultrasonic transducer and (ii) a time when an ultrasonic echo returns from the front surface of the object 216. Alternatively, the processor may measure a time difference between: (i) a time when an ultrasonic echo returns from an end of the delay line material 206 at the interface between the delay line material 206 and the liquid of the cavity 214 and (ii) a time when an ultrasonic echo returns from the front surface of the object 216. The measurement apparatus 202 may be programmed with the speed of sound in the delay line material 206 and the liquid, such that the processor can convert the echo return time or time difference into a distance. In this manner, the processor may be able to determine a distance to the surface of the object 216 for a plurality of points on the surface of the object 216 that correspond to each of the ultrasonic transducers of the two-dimensional ultrasonic transducer array 204. In some instances, the processor may also measure distances to damage beneath the surface of the object 216 using ultrasonic echoes received from beneath the surface of the object 216.

Figure 2B:
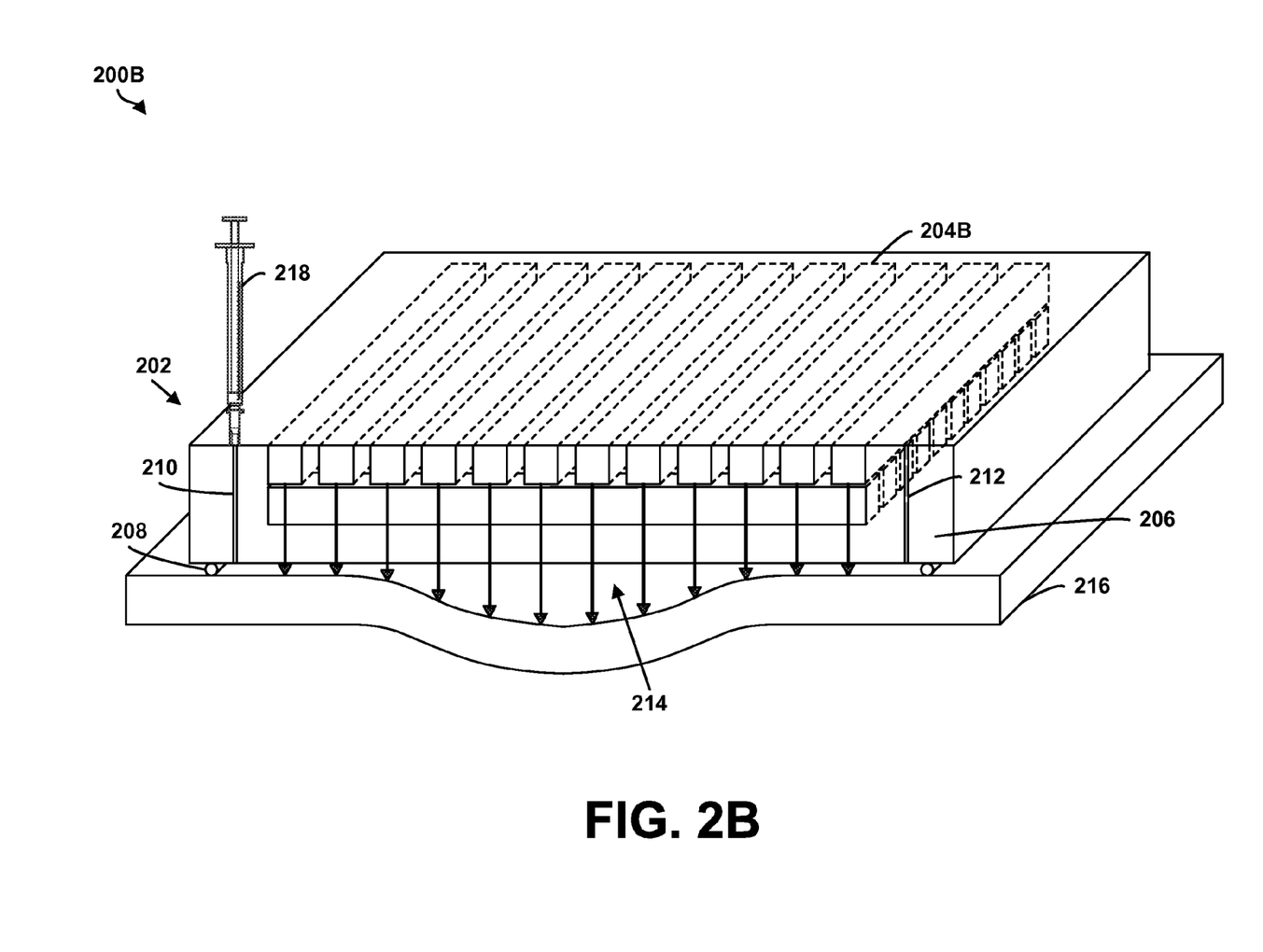

FIG. 2B FIG. 2A is an illustration of another example liquid-coupled system 200B. As shown in FIG. 2B, the example system 200B includes a measurement apparatus 202 having a two-dimensional ultrasonic transducer array 204B, a delay line material 206, a sealing member 208, a liquid inlet 210, and a liquid exhaust outlet 212.

The system 200B of FIG. 2B is similar to the system 200A of FIG. 2A, with the qualification that in the system 200B, the measurement apparatus 202 includes a two-dimensional ultrasonic transducer array 204B that is in the form of a two-dimensional matrix array. Thus, in line with the discussion above, the two-dimensional ultrasonic transducer array 204B is illustrated as including a first plurality of elongated electrodes arranged in a first orientation in a first layer, and a second plurality of elongated electrodes arranged in a second layer in a second orientation. As such, the first plurality of elongated electrodes intersects the second plurality of elongated electrodes, forming a matrix of individual transducer elements capable of emitting and receiving ultrasonic waves.

Figure 3A:
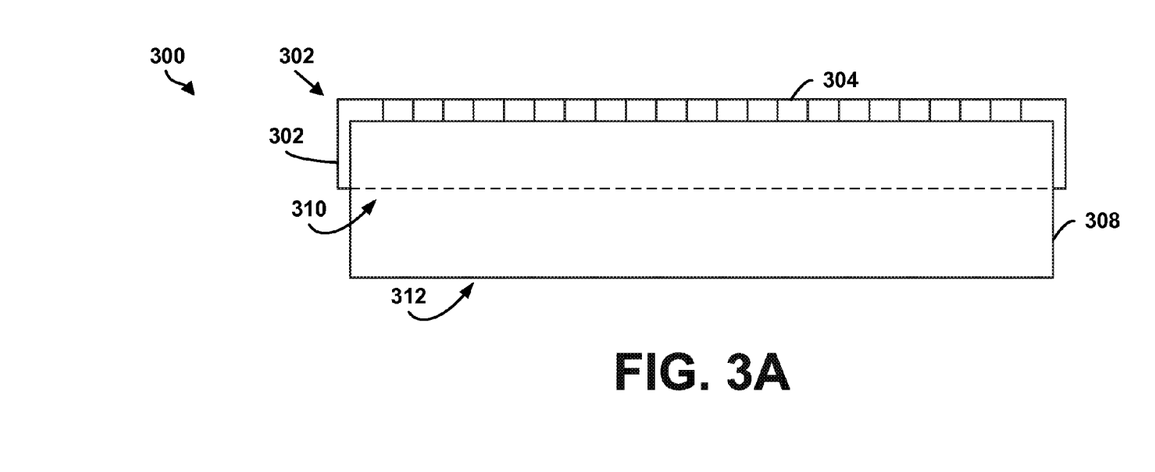
FIGS. 3A and 3B are conceptual illustrations of another example system according to an example embodiment.
Figure 3B:
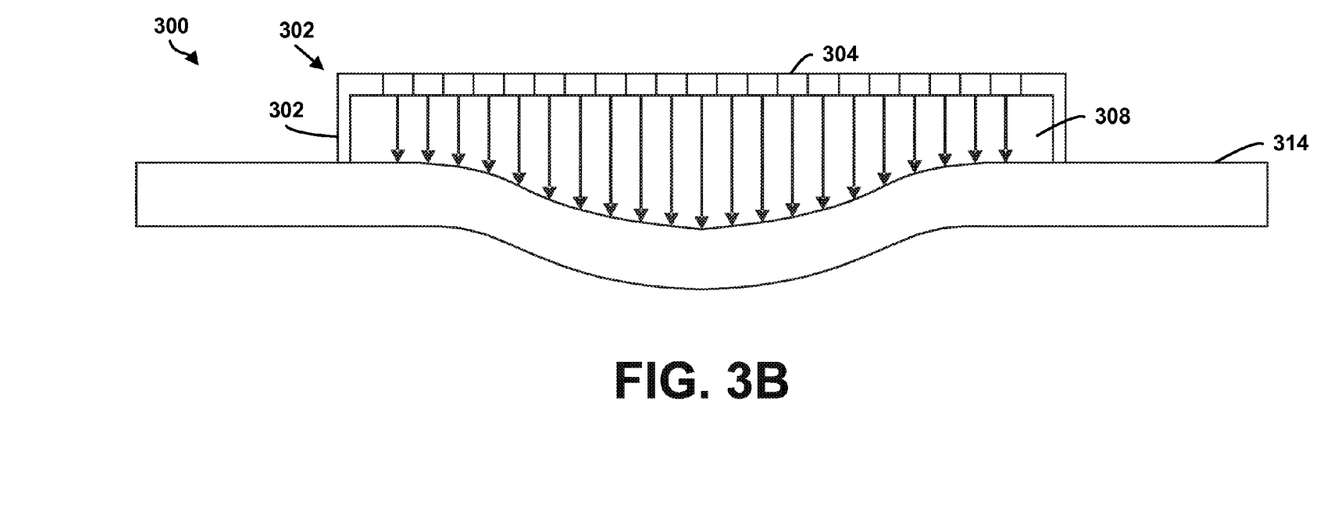

FIGS. 3A and 3B are illustrations of another example system 300. In particular, FIGS. 3A and 3B are illustrations of an example solid-coupling system 300 that uses a solid couplant rather than using a liquid couplant like the liquid-coupling system 200 of FIG. 2. As shown in FIGS. 3A and 3B, the example system 300 includes a measurement apparatus 302 having a housing 304, a two-dimensional ultrasonic transducer array 306, and an elastomeric delay line material 308.

The two-dimensional ultrasonic transducer array 306 may be similar to the two-dimensional ultrasonic transducer array 204A of FIG. 2A. Thus, although only a single row of ultrasonic transducers are visible in FIGS. 3A and 3B, the two-dimensional ultrasonic transducer array 306 includes multiple rows of ultrasonic transducers. Alternatively, the two-dimensional ultrasonic array 306 may be in the form of a two-dimensional matrix array that is similar to the two-dimensional ultrasonic array 204B of FIG. 2B (not shown).

The elastomeric delay line material 308 may be a semi-solid delay line material such as Aqualene. Aqualene is commonly used as a "hard water" material and has advantages in terms of acoustic impedance matching and coupling capability, especially to irregular surface contours.

As illustrated in FIG. 3A, the housing 304 has an opening 310 on one side, and the elastomeric delay line material 308 protrudes through the opening 310 when the elastomeric delay line material 308 is in a relaxed state. Further, the elastomeric delay line material 308 has a contact face 312 that is configured to be applied to a surface of an object.

As illustrated in FIG. 3B, in operation, an inspector may apply the contact face 312 of the elastomeric delay line material 308 to the surface of the object 314. The inspector may then continue to press the measurement apparatus 302 towards the surface of the object 314, causing a portion of the elastomeric delay line material 308 to compress as the elastomeric delay line material 308 conforms to the surface of the object 314. After the elastomeric delay line material 308 conforms to the surface of the object 314, the inspector may then press a button or otherwise trigger the ultrasonic transducers of the two-dimensional ultrasonic transducer array 306 to transmit ultrasonic pulses toward the surface of the object 314 through the elastomeric delay line material 308. Ultrasonic signals received from the two-dimensional ultrasonic transducer array 306 may then be stored and processed to construct a virtual representation of the surface and/or interior of the object 314 or to classify damage on the surface of the object 314 as acceptable or unacceptable and provide an output indicative of the classification.

In one example, for each of the ultrasonic transducers of the ultrasonic transducer array 306, a processor of the system 300 (not shown) may measure an echo return time between (i) a time when an initial ultrasonic pulse was transmitted by the ultrasonic transducer and (ii) a time when an ultrasonic echo returns from the front surface of the object 316. The measurement apparatus 302 may be programmed with the speed of sound in the elastomeric delay line material 308 (optionally calibrated for any changes in speed due to compression) and the liquid, such that the processor can convert the echo return time or time difference into a distance. In this manner, the processor may be able to determine a distance to the surface of the object 314 for a plurality of points on the surface of the object 314 that correspond to each of the ultrasonic transducers of the two-dimensional ultrasonic transducer array 304. In some instances, the processor may also measure distances to damage beneath the surface of the object 216 using ultrasonic echoes received from beneath the surface of the object.

Figure 4:
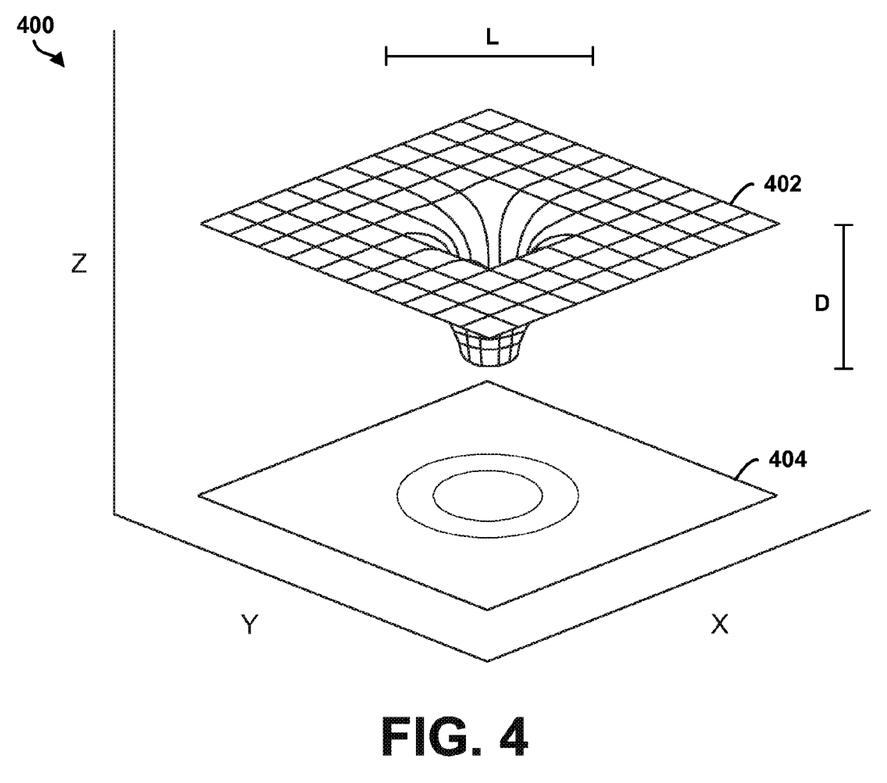
FIG. 4 is a conceptual illustration of a virtual representation of a surface of an object according to an example embodiment.

FIG. 4 is a conceptual illustration of a virtual representation 400 of a surface of an object. The virtual representation 400 is an example of a virtual representation that may be constructed using any of the example systems described herein, such as the example system 100 of FIG. 1, the example system 200 of FIG. 2, or the example system 300 of FIGS. 3A and 3B. Further, the virtual representation 400 is provided for purposes of example only, and is not meant to be limiting.

As shown in FIG. 4, the virtual representation 400 includes a three-dimensional (3D) surface plot 402 as well as a corresponding two-dimensional (2D) contour plot. Advantageously, an inspector may use the virtual representation to evaluate the profile and contour of a depression in the surface of an object. Further, the virtual representation 400 also includes an indication of a maximum depth (D) and a maximum width (W) of the depression for review by the inspector.

Figure 5:
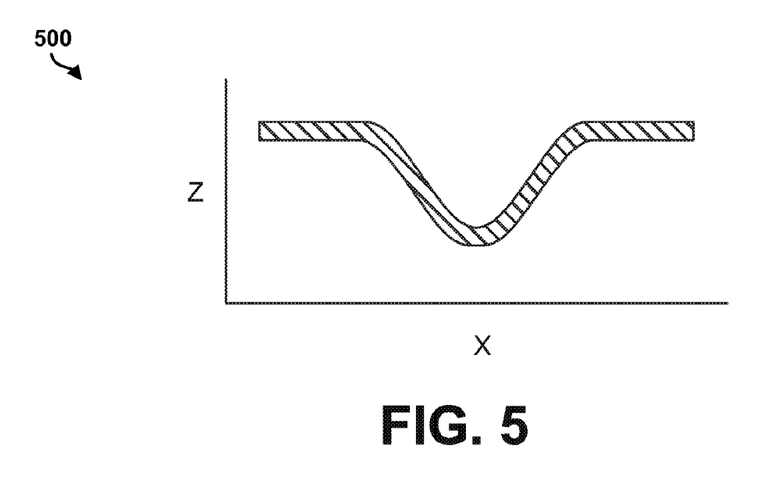
FIG. 5 is a conceptual illustration of another virtual representation of a surface of an object according to an example embodiment.

FIG. 5 is a conceptual illustration of another virtual representation 500 of a surface of an object. The virtual representation 500 is an example of another type of virtual representation that may be constructed by the example systems described herein. In particular, FIG. 5 illustrates a cross-sectional scan of a surface of an object. Note that although FIG. 5 depicts the cross-sectional scan as being along the x-axis, the systems disclosed herein may be configured to construct cross-sectional scans along any plane, since the systems are capable of capturing volumetric data.

In addition to the virtual representation 400 of FIG. 4 and the virtual representation 500 of FIG. 5, the systems disclosed herein may also be configured to construct other types of virtual representations, such as waveform plots representing ultrasonic signals.

Figure 6A:
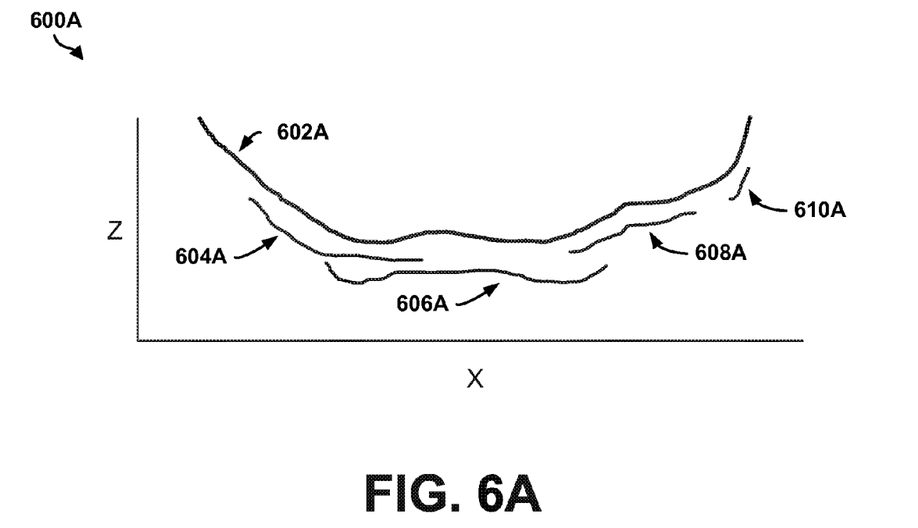
FIGS. 6A and 6B are illustrations of additional virtual representations of a surface of an object and beneath the surface of the object according to an example embodiment.
Figure 6B:
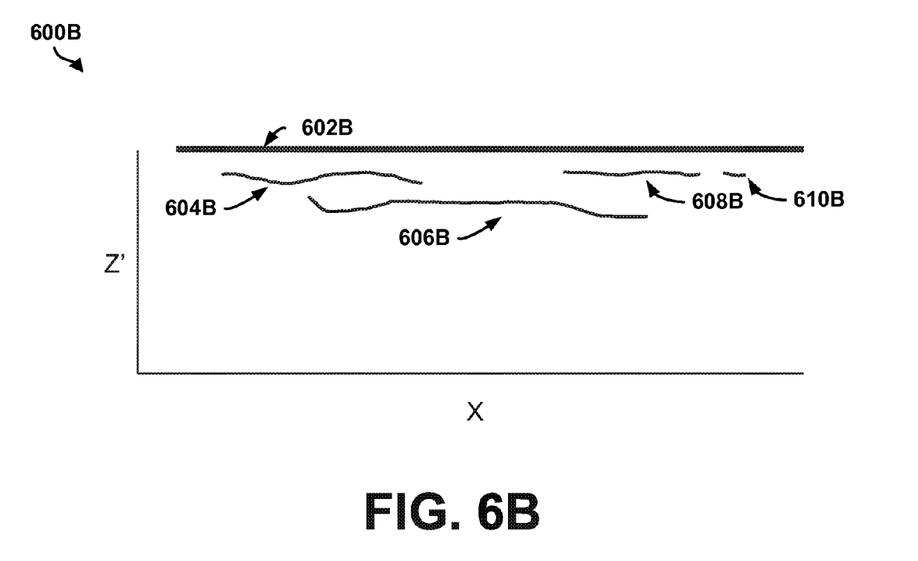

FIGS. 6A and 6B are illustrations of additional virtual representations of a surface of an object and beneath the surface of the object according to an example embodiment. As shown in FIG. 6A, a virtual representation 600A illustrates a cross-sectional scan of a surface of an object and an interior of the object. The virtual representation 600A depicts the surface 602A of an object as well as multiple indications 604A, 606A, 608A, 610A of damage beneath the surface 602A of the object.

Advantageously, an operator viewing the virtual representation 600A can analyze damage beneath the surface 602A of the object. By way of example, the surface 602A may be an aircraft structure (e.g., a fuselage), and the indications 604A, 606A, 608A, 610A may represent plies lying beneath surface resin pools. In some instances, the surface of the fuselage may have elongated pools of resin due to anomalies in the tooling and processing of the fuselage. Carbon fibers beneath these pools may have a bend in them, and thus, may be weaker than straight fibers when loads are applied. In such a scenario, the virtual representation 600A may enable an operator to measure how much of a bend exists in the carbon fibers within the fuselage.

Furthermore, in FIG. 6B, a virtual representation 600B illustrates an alternative cross-sectional scan of the surface of the object and the interior of the object that are depicted in FIG. 6A. As shown in FIG. 6B, the surface of the object has been flattened out by sliding all of the distances to points on the surface of the object to be the same depth. This normalizing process results in a normalized surface 602B that lies within a single plane that is parallel to the z-axis. Similarly, in the virtual representation 600B, the multiple indications 604A, 606A, 608A, 610A of damage of FIG. 6A have also been normalized, and are depicted as indications 606A, 606B, 608B, and 610B, respectively. In this manner, an operator can also use the virtual representation 600B to analyze damage beneath the surface of the object.

The virtual representation 600B of FIG. 6B is one example of a virtual representation depicting a normalized or flattened surface of an object. In other instances, other virtual representations having normalized or flattened surfaces may also be constructed and displayed. For example, virtual representations of time-based slices parallel to the normalized or flattened surface may be provided for display, either slice-by-slice, in three-dimensions, or in two-dimensions with damage beneath the surface projected onto a single image.

In some examples, a display interface may include an option that allows an operator to toggle between the virtual representation 600A of FIG. 6A, depicting the as-collected surface 602A, and the virtual representation 600B of FIG. 6B.

Figure 7:
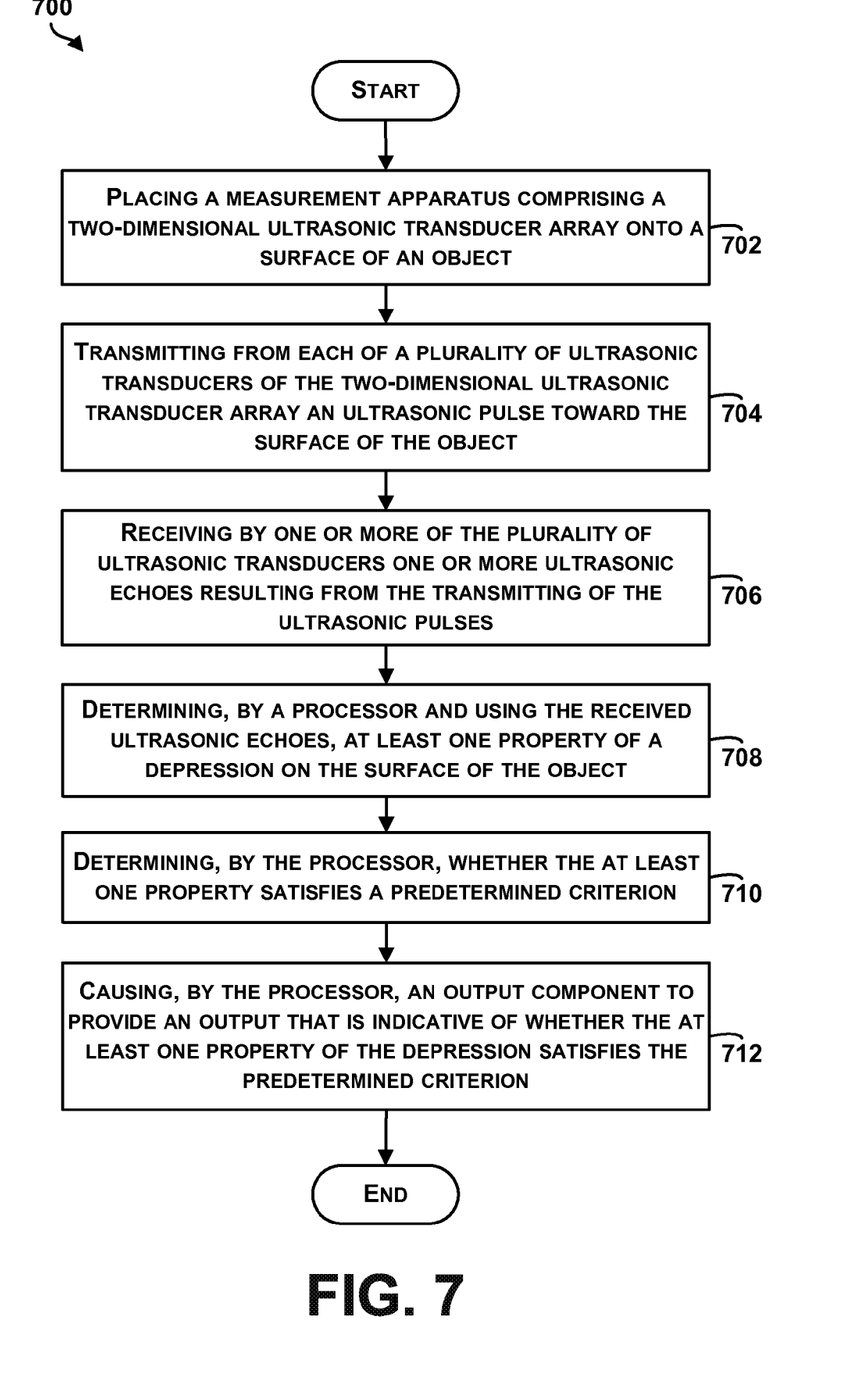
FIG. 7 is a flowchart of an example method for evaluating a surface of an object according to an example embodiment.

FIG. 7 is a flowchart of an example method 700 for evaluating a surface of an object. Method 700 shown in FIG. 7 present an embodiment of a method that, for example, could be used with the system shown in FIG. 1, for example, or any of the systems disclosed herein. Example devices or systems may be used or configured to perform logical functions presented in FIG. 7. In some instances, components of the devices and/or systems may be configured to perform the functions such that the components are actually configured and structured (with hardware and/or software) to enable such performance. In other examples, components of the devices and/or systems may be arranged to be adapted to, capable of, or suited for performing the functions. Method 700 may include one or more operations, functions, or actions as illustrated by one or more of blocks 702-712. Although these blocks are illustrated in a sequential order, these blocks may also be performed in parallel, and/or in a different order than those described herein. Also, the various blocks may be combined into fewer blocks, divided into additional blocks, and/or removed based upon the desired implementation.

It should be understood that for this and other processes and methods disclosed herein, flowcharts show functionality and operation of one possible implementation of present embodiments. In this regard, each block may represent a module, a segment, or a portion of program code, which includes one or more instructions executable by a processor for implementing specific logical functions or steps in the process. The program code may be stored on any type of computer readable medium or data storage, for example, such as a storage device including a disk or hard drive. The computer readable medium may include non-transitory computer readable medium or memory, for example, such as computer readable media that stores data for short periods of time like register memory, processor cache, and RAM. The computer readable media may also be any other volatile or non-volatile storage systems. The computer readable medium may be considered a tangible computer readable storage medium, for example.

In addition, each block in FIG. 7 may represent circuitry that is wired to perform the specific logical functions in the process. Alternative implementations are included within the scope of the example embodiments of the present disclosure in which functions may be executed out of order from that shown or discussed, including substantially concurrent or in reverse order, depending on the functionality involved, as would be understood by those skilled in the art.

Initially, at block 702, the method 700 includes placing a measurement apparatus comprising a two-dimensional ultrasonic transducer array onto a surface of an object. By way of example, an inspector may place any of the measurement apparatuses disclosed herein over a depression (e.g., a dent) on a surface of a structure such as an aircraft structure. If the inspector is using a measurement apparatus that is similar to the measurement apparatus 202 of FIG. 2, the inspector may place the measurement apparatus onto the surface of the object such that a sealing member forms a cavity between the measurement apparatus and the surface of the object. On the other hand, if the inspector is using a measurement apparatus that is similar to the measurement apparatus 302 of FIGS. 3A and 3B, the inspector may press the measurement apparatus towards the surface of the object such that an elastomeric delay line material conforms to the surface of the object. In some instances, an inspector may calibrate the measurement apparatus using a depression standard, prior to placing the measurement apparatus onto the surface of the object.

At block 704, the method 700 includes transmitting from each of a plurality of ultrasonic transducers of the two-dimensional ultrasonic transducer array an ultrasonic pulse toward the surface of the object. For instance, the inspector may press a button or perform another triggering mechanism that causes an array controller to energize each of the ultrasonic transducers to send an ultrasonic pulse.

At block 707, the method 700 includes receiving by one or more of the plurality of ultrasonic transducers one or more ultrasonic echoes resulting from the transmitting of the ultrasonic pulses. By way of example, each of the plurality of ultrasonic transducers may receive an ultrasonic echo from the front surface of the object. Further, in line with the discussion above, in some instances, each of the ultrasonic transducers may also receive another ultrasonic echo from an end of a delay line material. Alternatively, the plurality of ultrasonic transducers may include a plurality of transmitting transducers and a plurality of receiving transducers. In such a configuration, the plurality of transmitting transducers may each transmit an ultrasonic pulse. Each of the second plurality of receiving transducers may then receive one or more ultrasonic echoes resulting from the transmitting by one or more of the plurality of transmitting transducers.

At block 708, the method 700 includes determining, by a processor and using the received ultrasonic echoes, at least one property of a depression on the surface of the object. As discussed above, the processor may analyze an ultrasonic signal to measure the echo return time between: (i) a time when an initial ultrasonic pulse was transmitted and (ii) a time when an ultrasonic echo returns from the front surface of the object. Alternatively, the processor may analyze an ultrasonic signal to measure a time difference between: (i) a time when an ultrasonic echo returns from an end of a delay line material and (ii) a time when an ultrasonic echo returns from the front surface of the object. The processor may then convert the echo return time or measured time difference to a distance using the speed of sound in the material(s) through which the ultrasonic pulse was transmitted. Thus, the processor may determine a distance to the surface of the object at multiple points on the surface of the object. Given the determined distances, the processor may then determine at least one property of a depression on the surface of the object, such as a maximum depth, average depth, maximum width, average width, width over depth ratio, etc.

In some instances, the method 700 may also include imaging damage beneath the surface of the object using ultrasonic echoes received from beneath the surface of the object.

At block 710, the method 700 includes determining, by the processor, whether the at least one property satisfies a predetermined criterion. As one example, the processor may determine whether a maximum depth of the depression is greater than a depth threshold. As another example, the processor may determine whether a maximum width of the depression is greater than a width threshold. As still another example, the processor may determine whether a width over depth ratio exceeds a threshold ratio.

And at block 712, the method 700 includes causing, by the processor, an output component to provide an output that is indicative of whether the at least one property of the depression satisfies the predetermined criterion. For instance, if the at least one property of the depression does not satisfy the predetermined criterion, the processor may cause the output component to provide a negative output (e.g., provide a red light), whereas if the at least one property of the depression does satisfy the predetermined criterion, the processor may cause the output component to provide a position output (e.g., provide a green light). Thus, when using the method 700, the inspector may quickly be able to discern whether or not the damage is acceptable or unacceptable.

Figure 8:
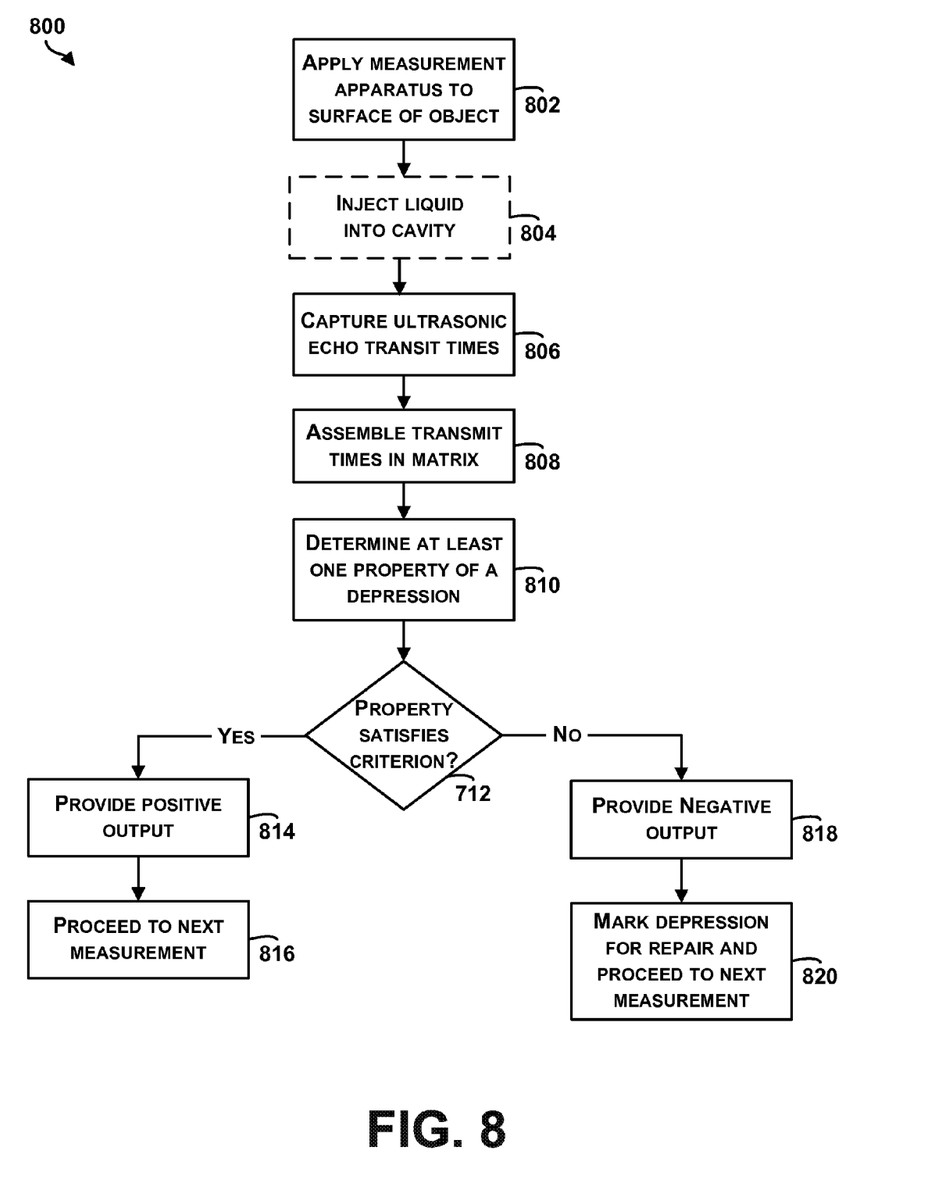
FIG. 8 is a flowchart of another example method for evaluating a surface of an object according to an example embodiment.

FIG. 8 is a flowchart of another example method 800 for evaluating a surface of an object according to an example embodiment. Method 800 shown in FIG. 8 present an embodiment of a method that, for example, could be used with the system 100 shown in FIG. 1, for example, or any of the systems disclosed herein.

Method 800 may include one or more operations, functions, or actions as illustrated by blocks 802-822 of the flowchart. Although the blocks are illustrated in a sequential order, these blocks may also be performed in parallel, and/or in a different order than those described herein. Also, the various blocks may be combined into fewer blocks, divided into additional blocks, and/or removed from the flowchart, based upon the desired implementation of the method 800. Each block may represent a module, segment, or a portion of program code, which includes one or more instructions executable by a processor for implementing specific logical functions or steps in the process. In addition, each block in FIG. 8 may represent circuitry that is wired to perform the specific logical functions in the process.

Initially, at block 802, the method 800 involves applying a measurement apparatus to a surface of an object. Optionally, at block 804, the method 800 may then involve injecting liquid into a cavity if the measurement apparatus is configured for liquid-coupling.

At block 806, the method then involves capturing ultrasonic echo transit times. For instance, each of a plurality of ultrasonic transducers of the measurement apparatus may transmit an ultrasonic pulse toward the surface of the object, and the ultrasonic transducer may then receive one or more ultrasonic echoes resulting from the transmission of the ultrasonic pulse. A processor may then use the received ultrasonic echoes to measure echo transmit times (e.g., echo return times or time differences between multiple echo return times) to determine a distance to the surface of the object for multiple points on the surface of the object.

At block 808, the processor may then assemble the echo transmit times in a matrix such as an x-y matrix and store the echo transmit times in a memory. Further, at block 810, the processor may determine at least one property of a depression on the surface of the object. For instance, the processor may convert the echo transmit times to distances, and use the determined distances to determine a maximum depth and/or maximum width of the depression.

Still further, at block 812, the processor may determine whether the at least one property satisfies a predetermined criterion. If the at least one property satisfies the predetermined criterion, then, at block 814, the processor may cause an output component to provide a positive output and, at block 816, an inspector may proceed to inspecting another depression on the surface of the object. Whereas, if the at least one property does not satisfy the predetermined criterion, then, at block 818, the processor may cause the output component to provide a negative output and, at block 820, the inspector may mark the damage for repair and proceed to inspecting another depression on the surface of the object.

The description of the different advantageous arrangements has been presented for purposes of illustration and description, and is not intended to be exhaustive or limited to the embodiments in the form disclosed. Many modifications and variations will be apparent to those of ordinary skill in the art. Further, different advantageous embodiments may provide different advantages as compared to other advantageous embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. A system for non-destructive evaluation of depressions on a surface of an object, the system comprising:
    a measurement apparatus comprising:
        a two-dimensional ultrasonic transducer array,
        a delay line material coupled to the two-dimensional ultrasonic transducer array,
        a sealing member positioned such that the sealing member forms a cavity between the delay line material and the surface of the object when the measurement apparatus is placed onto the surface of the object, and
        a liquid inlet for injecting a liquid into the cavity; and
    a processor configured to determine, using ultrasonic signals received from the two-dimensional ultrasonic transducer array, at least one property of a depression on the surface of the object.

2. The system of claim 1, further comprising an output component,
wherein the processor is further configured to:
determine whether the at least one property of the depression satisfies at least one predetermined criterion, and
cause the output component to provide an output that is indicative of whether the at least one property of the depression satisfies the predetermined criterion.

3. The system of claim 2:
wherein the at least one property of the depression comprises a maximum depth of the depression, and
wherein the predetermined criterion comprises a threshold depth criterion.

4. The system of claim 2:
wherein the at least one property of the depression comprises a maximum width of the depression, and
wherein the predetermined criterion comprises a threshold width criterion.

5. The system of claim 1, wherein the measurement apparatus and the processor are part of a handheld device.

6. The system of claim 1, wherein the measurement component further comprises a liquid exhaust outlet having a check valve.

7. The system of claim 1, wherein the processor is further configured to:
determine, using the ultrasonic signals received from the two-dimensional ultrasonic transducer array, a distance to the surface of the object for a plurality of points on the surface of the object, and
determine the at least one property of the depression on the surface of the object based on determined distances to the plurality of points on the surface of the object.

8. The system of claim 7:
wherein the two-dimensional ultrasonic transducer array comprises a plurality of ultrasonic transducers,
wherein the ultrasonic signals comprise ultrasonic signals received from each of the plurality of transducers, and
wherein determining the distance to the surface of the object for the plurality of points on the surface of the object comprises determining, for each of one or more of the plurality of ultrasonic transducers, a time difference between an echo received by the ultrasonic transducer from an end of the delay line material and an echo received from the surface of the object.

9. The system of claim 7, further comprising a display component,
wherein the processor is further configured to:
construct a virtual representation of the surface of the object based on the determined distances to the plurality of points on the surface of the object, and
provide the virtual representation of the surface of the object to the display component for display.

10. The system of claim 1, wherein the processor is further configured to determine, using the ultrasonic signals received from the two-dimensional ultrasonic transducer array, a distance to damage beneath the surface of the object.

11. A system for non-destructive evaluation of depressions on a surface of an object, the system comprising:
a measurement apparatus comprising:
a housing having an opening,
a two-dimensional ultrasonic transducer array positioned within the housing, and
an elastomeric delay line material coupled to the two-dimensional ultrasonic transducer array, the elastomeric delay line material having a contact face configured to contact the surface of the object,
wherein the contact face of the elastomeric delay line material protrudes through the opening of the housing when the elastomeric delay line material is in a relaxed state, and
wherein the elastomeric delay line material is compressible toward the two-dimensional ultrasonic transducer array when the measurement apparatus is placed onto the surface of the object; and
a processor configured to determine, using ultrasonic signals received from the two-dimensional ultrasonic transducer array, at least one property of a depression on the surface of the object.

12. The system of claim 11, further comprising an output component,
wherein the processor is further configured to:
determine whether the at least one property of the depression satisfies a predetermined criterion, and
cause the output component to provide an output that is indicative of whether the at least one property of the depression satisfies the predetermined criterion.

13. The system of claim 11, wherein the measurement apparatus is coupled to a robotic inspection device.

14. The system of claim 11, wherein the processor is further configured to:
determine, using the ultrasonic signals received from the two-dimensional ultrasonic transducer array, a distance to the surface of the object for a plurality of points on the surface of the object, and
determine the at least one property of the depression on the surface of the object based on determined distances to the plurality of points on the surface of the object.

15. The system of claim 14:
wherein the two-dimensional ultrasonic transducer array comprises a plurality of ultrasonic transducers,
wherein the ultrasonic signals comprise ultrasonic signals received from each of the plurality of transducers, and
wherein determining the distance to the surface of the object for the plurality of points on the surface of the object comprises determining, for each of one or more of the plurality of ultrasonic transducers, a time difference between an initial pulse transmitted by the ultrasonic transducer and an echo received by the ultrasonic transducer from the surface of the object.

16. The system of claim 14, further comprising a display component,
wherein the processor is further configured to:
construct a virtual representation of the surface of the object based on the determined distances to the plurality of points on the surface of the object, and
provide the virtual representation of the surface of the object to the display component for display.

17. A method for non-destructive evaluation of depressions on a surface of an object, the method comprising:
placing a measurement apparatus comprising a two-dimensional ultrasonic transducer array onto the surface of the object;
transmitting from each of a plurality of ultrasonic transducers of the two-dimensional ultrasonic transducer array an ultrasonic pulse toward the surface of the object;
receiving by one or more of the plurality of ultrasonic transducers one or more ultrasonic echoes resulting from the transmitting of the ultrasonic pulses;
determining, by a processor and using the received ultrasonic echoes, at least one property of a depression on the surface of the object;

determining, by the processor, whether the at least one property satisfies a predetermined criterion; and causing, by the processor, an output component to provide an output that is indicative of whether the at least one property of the depression satisfies the predetermined criterion.

18. The method of claim 17:

wherein placing the measurement apparatus onto the surface of the object forms a cavity between the measurement apparatus and the surface of the object, and wherein the method further comprises injecting a liquid into the cavity before transmitting the ultrasonic pulse from each of the plurality of ultrasonic transducers.

19. The method of claim 17, further comprising:

determining, using the received ultrasonic echoes, a distance to the surface of the object for a plurality of points on the surface of the object, and determining the at least one property of the depression on the surface of the object based on determined distances to the plurality of points on the surface of the object.

20. The method of claim 19, further comprising:

constructing a virtual representation of the surface of the object based on the determined distances to the plurality of points on the surface of the object, and providing the virtual representation of the surface of the object for display.

* * * * *